United States Patent
Kulesza

(10) Patent No.: US 10,500,279 B2
(45) Date of Patent: Dec. 10, 2019

(54) LOW TOXICITY TOPICAL ACTIVE AGENT DELIVERY SYSTEM

(71) Applicant: John E. Kulesza, Berlin, CT (US)

(72) Inventor: John E. Kulesza, Berlin, CT (US)

( * ) Notice: Subject to any disclaimer, the term of this patent is extended or adjusted under 35 U.S.C. 154(b) by 0 days.

(21) Appl. No.: 15/890,408

(22) Filed: Feb. 7, 2018

(65) Prior Publication Data

US 2018/0161435 A1 Jun. 14, 2018

Related U.S. Application Data

(63) Continuation of application No. 13/685,244, filed on Nov. 26, 2012, which is a continuation of application No. 12/711,381, filed on Feb. 24, 2010, now Pat. No. 8,337,870.

(60) Provisional application No. 61/286,668, filed on Dec. 15, 2009.

(51) Int. Cl.

| A61K 31/192 | (2006.01) |
|---|---|
| A61K 31/194 | (2006.01) |
| A61K 31/203 | (2006.01) |
| A61K 8/58 | (2006.01) |
| A61Q 19/00 | (2006.01) |
| A61K 47/08 | (2006.01) |
| A61K 9/00 | (2006.01) |
| A61K 31/07 | (2006.01) |
| A61K 31/60 | (2006.01) |
| A61K 8/368 | (2006.01) |
| A61K 8/38 | (2006.01) |
| A61K 8/67 | (2006.01) |
| A61Q 19/08 | (2006.01) |
| A61K 8/69 | (2006.01) |
| A61Q 15/00 | (2006.01) |
| A61K 47/24 | (2006.01) |

(52) U.S. Cl.
CPC .............. *A61K 47/08* (2013.01); *A61K 8/368* (2013.01); *A61K 8/38* (2013.01); *A61K 8/585* (2013.01); *A61K 8/671* (2013.01); *A61K 8/69* (2013.01); *A61K 9/0014* (2013.01); *A61K 31/07* (2013.01); *A61K 31/192* (2013.01); *A61K 31/194* (2013.01); *A61K 31/203* (2013.01); *A61K 31/60* (2013.01); *A61Q 15/00* (2013.01); *A61Q 19/00* (2013.01); *A61Q 19/007* (2013.01); *A61Q 19/08* (2013.01); *A61K 47/24* (2013.01)

(58) Field of Classification Search
CPC . A61K 8/585; A61K 8/69; A61K 8/70; A61K 31/203; A61K 31/07; A61K 31/192; A61K 31/194

See application file for complete search history.

(56) References Cited

U.S. PATENT DOCUMENTS

| 4,725,429 A | 2/1988 | Scott et al. |
|---|---|---|
| 4,727,088 A | 2/1988 | Scott et al. |
| 4,826,828 A | 5/1989 | Wilmott et al. |
| 4,888,363 A | 12/1989 | Dulak et al. |
| 5,118,507 A | 6/1992 | Clement |
| 5,837,223 A | 11/1998 | Barone et al. |
| 5,955,097 A | 9/1999 | Tapolsky et al. |
| 6,224,851 B1 | 5/2001 | Bara |
| 6,251,375 B1 | 6/2001 | Bara |
| 6,395,285 B1 | 5/2002 | Lorant |
| 6,573,235 B1 | 6/2003 | Surbled et al. |
| 6,890,519 B2 | 5/2005 | Mercier et al. |
| 7,776,348 B2 | 8/2010 | Gardel et al. |
| 8,337,870 B2 * | 12/2012 | Kulesza ............... A61K 9/0014 424/401 |
| 2001/0005503 A1 | 6/2001 | Bara |
| 2001/0041168 A1 | 11/2001 | Ramin |
| 2002/0022040 A1 | 2/2002 | Robinson et al. |
| 2002/0110572 A1 | 8/2002 | Chandar et al. |
| 2002/0136745 A1 | 9/2002 | Calello et al. |
| 2002/0137642 A1 | 9/2002 | Lorant |
| 2004/0197284 A1 | 10/2004 | Auguste |
| 2005/0008592 A1 | 1/2005 | Gardel et al. |
| 2005/0069564 A1 | 3/2005 | Eversheim et al. |
| 2006/0135822 A1 | 6/2006 | Schwartz et al. |
| 2006/0147383 A1 | 7/2006 | Mallard et al. |
| 2006/0204530 A1 | 9/2006 | Ramirez |
| 2007/0003536 A1 | 1/2007 | Zimmerman et al. |
| 2007/0189988 A1 | 8/2007 | Golz-Berner et al. |
| 2009/0270298 A1 | 10/2009 | Compain |
| 2010/0216757 A1 | 8/2010 | Mallard et al. |

FOREIGN PATENT DOCUMENTS

| AU | 2004-248926 A1 | 12/2004 |
|---|---|---|
| BR | 9805691 A | 5/2000 |
| BR | PI040951 A | 4/2006 |
| CA | 2256080 A1 | 6/1999 |

(Continued)

OTHER PUBLICATIONS

Strakosch, Arch Derm Syphilol, 47: 16-26 (1943) Abstract Only.
Pubchem ID 62427, "phenyl trimethicone" accessed at https://pubchem.ncbi.nlm.nih.gov/compound/Phenyltris_trimethylsiloxy_silane#section=Top on Nov. 28, 2016.
Creations Couleurs, Water Free Emulsions Formulary Oct. 2000.
Lotioncrafter 1550, Phenyl trimethicone, downloaded from http://lotioncrafter.com/reference/tech_data_1550.pdf.

(Continued)

*Primary Examiner* — Lakshmi S Channavajjala
(74) *Attorney, Agent, or Firm* — Dinsmore & Shohl LLP; Weston R. Gould

(57) ABSTRACT

An active agent delivery composition is provided that allows topical delivery of active agents including vitamin A and its derivatives. A polyhalogenic vehicle serves as a coupler for an active agent and a silicone carrier so as to allow solubilization of active agents not normally miscible in silicones and providing a moisture maintaining composition.

19 Claims, No Drawings

(56) References Cited

FOREIGN PATENT DOCUMENTS

| | | | |
|---|---|---|---|
| CA | 2526642 | A1 | 12/2004 |
| CN | 1223854 | A | 7/1999 |
| CN | 1223855 | A | 7/1999 |
| CN | 1237959 | A | 12/1999 |
| CN | 1471903 | A | 2/2004 |
| CN | 1809363 | A | 7/2006 |
| DE | 69805494 | T2 | 10/2003 |
| DE | 102004045411 | A1 | 3/2006 |
| EP | 0930058 | A1 | 7/1999 |
| EP | 0930059 | A1 | 7/1999 |
| EP | 0968709 | A1 | 1/2000 |
| EP | 1064989 | A | 1/2001 |
| EP | 1374835 | A | 1/2004 |
| EP | 1641463 | A1 | 4/2006 |
| ES | 2178132 | T3 | 12/2002 |
| ES | 2322269 | T3 | 6/2009 |
| FR | 2768925 | A1 | 4/1999 |
| FR | 2773064 | A1 | 7/1999 |
| FR | 2831444 | A1 | 5/2003 |
| FR | 2856301 | A1 | 12/2004 |
| JP | 04-373141 | A | 12/1992 |
| JP | 03400732 | A | 9/1999 |
| JP | 03452820 | A | 9/1999 |
| JP | 11263709 | A | 9/1999 |
| JP | 11263710 | A | 9/1999 |
| JP | 2004-026833 | A | 1/2004 |
| JP | 2008137991 | A | 6/2008 |
| KR | 10-042066 | A | 1/2004 |
| MX | PA05013232 | A | 3/2006 |
| WO | 0064472 | A1 | 11/2000 |
| WO | 2004112798 | A | 12/2004 |
| WO | 2006094551 | A1 | 9/2006 |
| WO | 2006111666 | A1 | 10/2006 |
| WO | 2008049401 | A2 | 5/2008 |
| WO | 2009063068 | A | 5/2009 |

OTHER PUBLICATIONS

Garaud, Dow Corning Europe, Chapter 16, downloaded from http://dowcorning.comcontent/publishededit/chapter16.pdf, Jul. 11, 2015.
Google Patent Search Translation of Susilo WO2008049401 A2, downloaded Jul. 12, 2015.
3M Cosmetic Fluids CF-61 and CF-76; Product Information; pp. 1-7.

* cited by examiner

LOW TOXICITY TOPICAL ACTIVE AGENT DELIVERY SYSTEM

CROSS REFERENCE TO RELATED APPLICATIONS

This application is a continuation of U.S. patent application Ser. No. 13/685,244 filed Nov. 26, 2012, that is a continuation of U.S. patent application Ser. No. 12/711,381 filed Feb. 24, 2010, and claims priority from U.S. Provisional Application No. 61/286,668 filed Dec. 15, 2009, the entire contents of each of which are incorporated herein by reference.

FIELD OF THE INVENTION

The invention relates to compositions for topical delivery of active agents. The compositions relate to delivery of active agents to the skin with reduced toxicity such as drying, irritation, or inflammation. The inventive composition is related to delivery of topical agents such as retinoids to the skin.

BACKGROUND OF THE INVENTION

Lipophilic skin care active agents such as retinoids are generally applied topically to reduce the appearance of aging, for other cosmetic purposes, or to treat a skin condition such as acne.

The comfort associated with application of topical agents is related in part to the rate of evaporation of the applied composition on the skin. A product with a slow evaporation rate could feel greasy on the skin whereas a product with an overly rapid evaporation rate feels either as if it has not been applied to the skin at all or leaves the user with the impression that not enough has been applied possibly leading to overuse. Combining topical agents with volatile silicones allows the proper evaporation rate to provide a pleasing application. Silicones, however, by themselves are poor solvents for hydrophobic organic active agents.

To address the poor solubility in silicones, delivery systems for these agents commonly require 35% or more organic solvent as a carrier to solubilize the active agent as well as provide suitability for combination with volatile compounds that provide pleasing application by the user. The prior art prefers alcohols such as ethyl alcohol as an organic solvent.

Many active agents contribute to thinning or drying of the skin. This problem is worsened by including significant levels of organic solvents that themselves can alter epidermal barrier lipids and contribute to skin irritation. Ethyl alcohol, as used in the retinoid composition of U.S. Pat. No. 4,826,828, incorporated herein by reference, was believed to be the solution for topical delivery of hydrophobic agents. Ethyl alcohol, to the contrary, contributes to skin irritation and dryness. Thus, combining ethyl alcohol with potentially irritating active agents increases skin dryness leading to non-optimal use.

Thus, there exists a need for a hydrophobic active agent delivery system that provides pleasing application and does not contribute to toxicity.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

An active agent delivery composition is provided that creates pleasing administration of an active agent to the skin of a subject without a greasy feeling residue. An inventive composition includes an active agent illustratively: vitamin A or its derivatives; hydroxy acids; benzoyl peroxide; resorcinol; antimicrobials; anti-neoplastic agents; anti-viral agents; nonsteroidal anti-inflammatory agents; UV filters; lipids; and immunomodulators. An active agent is optionally vitamin A or a derivative thereof present at between 0.001 to 2 weight percent. Optionally, a vitamin A derivative is retinal, retinoic acid, retinyl ester, retinol, tretinoin, isotretinoin, adapalene, tazarotene, or combinations thereof. An active agent is optionally salicylic acid, acetylsalicylic acid, or combinations thereof.

The inventive composition provides for pleasing skin administration through the use of a silicone carrier that is optionally a linear aliphatic polyorganosiloxane, optionally ethyl trisiloxane.

A polyhalogenic vehicle is present in the inventive composition to solubilize the active agent with the carrier while reducing or eliminating the need for an organic solvent such as ethanol. A vehicle is optionally a perfluoro ether, optionally, methoxynonafluorobutane or ethoxynonafluorobutane. The vehicle is optionally present from about 15 to 25 percent by weight.

An optional organic solvent is included. Optionally, the organic solvent is present at less than 25 percent by weight. Optionally, the organic solvent is present at less than 5 percent by weight.

Also provided is a process of treating a skin condition in a subject. The skin condition may be, for example, acne, wrinkles, dryness, cancer, or perspiration. The inventive process includes applying an inventive composition to the skin of a subject.

DETAILED DESCRIPTION OF THE PREFERRED EMBODIMENTS

It is to be understood that the present invention is not limited to particular embodiments described, which may, of course, vary. It is also to be understood that the terminology used herein is for the purpose of describing particular embodiments only and is not intended to be limiting.

The invention has utility for topical delivery of active agents. The invention has more specific utility for the delivery of hydrophobic active agents to the skin with reduced agent or solvent related side effects and improved comfort and user compliance.

The inventive composition includes an active agent combined with a carrier and a compatible vehicle.

As used herein the term "active agent" refers to a molecule suitable for delivery to the skin or mucosal regions of a subject. Optionally, an active agent has pharmaceutical activity and is present for the treatment or prevention of a skin condition. Active agents are optionally low polarity molecules such as those having a hydrocarbon chain of three or more carbons, but may also comprise materials of higher polarity. Examples of active agents illustratively include: vitamin A or its derivatives; hydroxy acids; aromatic molecules such as benzoyl peroxide and resorcinol; antimicrobials such as azelaic acid, erythromycin, sodium sulfacetamide, tetracycline and derivatives, and clindamycin; anti-neoplastic agents and/or ophthalmic agents illustratively including 5-fluorouracil, doxorubicin, imiquimod, and sodium [o-(2,6-dichloranilino) phenyl] acetate; anti-viral agents illustratively ganciclovir, trifluorothymidine and related compounds; nonsteroidal anti-inflammatory agents illustratively flurbiprofen, ibuprofen, naproxen, indomethacin and related compounds; anti-mitotic drugs illustratively colchicine taxol and related compounds; drugs that act on actin polymerization illustratively phalloidin, cytochlasin B and related compounds; inhibitors of dihydropyrimidine dehydrogenase (DPD), thymidine phosphorylase (TP) and/or uridine phosphorylase (UP) enzyme inhibitors; ultraviolet light (UV) filters illustratively benzophenone derivatives such as oxybenzone, octocrylene, octyl methoxycinnamate, and avobenzone; radiation proactive agents illustratively methyluracils such as 6-methyluracil and 4-methyluracil; and immunomodulating molecules such as tacrolimus, and pimecrolimus. An active agent need not have pharmaceutical activity. Other active agents are illustratively cosmetics such as pigments, dyes, and fillers. It is appreciated that an inventive composition optionally includes more than one active agent. Optionally, 2, 3, 4, 5, 6, or more active agents are present in an inventive composition. An active agent is optionally a prodrug that is converted to a desired active species optionally in the skin or layer thereof.

An active agent is optionally a lipid such as those suitable for controlling perspiration. Lipids optionally have an HLB of less than about 12, less than about 8, or optionally less than about 6. Illustrative examples of lipids include glyceryl monostearate, glyceryl monoisostearate, glyceryl monomyristate, glyceryl monoleate, diglyceryl monoisostearate, propylene of glycol monostearate, propylene glycol monoisostearate, propylene glycol monocaprylate, sorbitan monoisostearate, sorbitan monocaprylate, sorbitan monoisooleate, glyceryl monolaurate, glyceryl monocaprylate, glyceryl monocaprate, mixtures thereof or the like. Optionally, the lipid is glyceryl monolaurate, made available by suppliers like Fitz Chem Corporation under the name MONOMULS 90-L12.

Typically, the lipid makes up from about 4 to about 35%, and optionally, from about 5 to about 20%, and optionally, from about 10 to about 15% by weight of the composition, based on total weight of the composition and including all ranges subsumed therein.

Examples of pigments illustratively include inorganic or organic molecules such as molecules in the form of metal lakes. Pigments are illustratively made of titanium dioxide, zinc oxide, D&C Red No. 36 and D&C Orange No. 17, calcium lakes of D&C Red No. 7, 11, 31 and 34, barium lake of D&C Red No. 12, D&C Red No. 13 strontium lake, aluminum lakes of FD&C Yellow No. 5, of FD&C Yellow No. 6, of D&C Red No. 27, of D&C Red No. 21 and of FD&C Blue No. 1, iron oxides, manganese violet, chromium oxide and ultramarine blue.

Examples of vitamin A or its derivatives illustratively include retinoids such as retinal, retinoic acid, retinyl ester, retinol, tretinoin, isotretinoin, adapalene, tazarotene, and the like.

Examples of hydroxy acids illustratively include beta hydroxy acids such as salicylic acid, acetylsalicylic acid, and the like.

While the description uses retinol as an illustrative example of an active agent, the specification is not limited as such. Other active agents are similarly operable herein.

Numerous skin or systemic conditions are treatable with the inventive composition illustratively including acne, wrinkles, dryness, eczema, psoriasis, actinic and nonactinic keratoses, rosaceous, among others. U.S. Pat. No. 3,932,665 described retinal as a therapeutic agent in a method for treating acne by topical application. The disclosure of U.S. Pat. No. 3,932,665 is accordingly hereby incorporated by reference. The topical administration of 5-fluorouracil for treatment of keratoses is described in U.S. Pat. No. 4,034,114, the contents of which are incorporated herein by reference. The inventive composition reduces the associated side effects that typically accompany topical or ophthalmologic administration of active agents.

The inventive composition is suitable for topical delivery of an active agent. The inventive composition illustratively includes a retinol formulated in a carrier containing volatile silicone. With such a carrier, retinol levels needed to achieve beneficial effects are minimized and the potential for irritant effects to the skin by retinol are greatly diminished. Moreover, retinol is stable when formulated in the silicone containing compositions of the invention in contrast to other conventional carriers.

The compositions of the invention may include 0.005 to 1.0 weight percent retinol, in which case they are optionally applied directly to the skin, or supplied as more concentrated solution containing higher levels of active agent, in which case prior to application they are diluted optionally by means of a cosmetically acceptable carrier to a desired level such as 0.005 to 1.0 weight percent for retinol. In the formulations of the invention, water is optionally minimized or eliminated to improve the stability of retinol and to minimize the potential for separation of the oil and water. Optionally, water is present at less than 2%. One of ordinary skill in the art will recognize that differing levels of active agent will be operable herein depending on the desired final amount of active agent.

Optionally, active agent is present in less than 30 percent w/w amounts. Optionally, active agent is present at a weight percent of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.1, 0.01, 0.001, 0.0001, any level in between or any range therein. Optionally, active agent is present at 20 percent w/w. Illustratively, when azelaic acid is an active agent it is present at 15 to 25 percent w/w. A vitamin A derivative is optionally present at 0.001 to 2 percent by weight. Imiquimod is optionally present at 3 to 8 percent by weight. Benzoyl peroxide is optionally present at 1 to 10 percent by weight. It is within the skill of the art to determine the optimal level of active agent in either a concentrated solution or a final solution for application.

An active agent is preferably provided in a carrier. A carrier is optionally present from 10 to 75 percent w/v. Carriers are optionally volatile compounds such as volatile silicones. Silicones are illustratively cyclic silicones or non-cyclic silicones. Examples of cyclic silicones illustratively include cyclic polydiorganosiloxanes, cyclotetradimethicones and cyclopentadimethicones. Linear organopolysiloxanes are illustratively alkyl-, alkoxy- or phenyldimethicones, and alkyl-, alkoxy- or phenyltrimethicones. Optionally, a carrier is an aliphatic volatile silicone. Aliphatic volatile silicones optionally have from two to six silicon atoms. Optionally, an aliphatic volatile silicone is a linear polyorganosiloxane such as a polyorganosiloxane with 2 to 6 silicon atoms, optionally, trisiloxane. Optionally, a carrier is ethyl trisiloxane. It is appreciated that an inventive composition optionally includes more than one carrier.

Volatile silicones optionally are lightweight carriers that evaporate on application and thus have an elegant, lightweight "feel" on the skin. Volatile silicones are typically limited in their ability to dissolve low polarity (i.e. usually greater than C7-C8)) organic compounds like retinoids. For example, when relatively low therapeutic levels of retinol (0.1-0.2% w/v) are dissolved in cyclomethicone alone, hazy solutions result due to incomplete solubilization by the silicone fluid.

Among the nearly infinite possibilities of vehicles that could function with both an active agent and a volatile silicone, it was unexpectedly discovered that an organic polyhalogenic vehicle could incorporate a retinoid at appropriate therapeutic levels and reduces the levels of hydrocarbon solvent to less than 5 percent in contrast to U.S. Pat. No. 4,826,828 which required 35-60 percent w/w hydrocarbon solvent. This discovery is interesting due to the fact that organic polyhalogenic vehicles are poor solubilizers of molecules such as retinoid on their own. Combined with the knowledge that silicones are poor solvents, one or ordinary skill in the art has no expectation of success combining two poor solubilizers to form a system that effectively solubilizes active agents. Organic polyhalogenic solvents are optionally those disclosed in U.S. Pat. No: 6,251,375, the contents of which are incorporated herein by reference. In particular instances, vehicles incorporate a halogen such as one or more fluorine atoms. In some specific instances, a vehicle is a perfluoro ether. In some particular instances, a vehicle is methoxynonafluorobutane or ethoxynonafluorobutane available from 3M Specialty Materials, St. Paul, Minn. A vehicle optionally has a boiling point less than 78° C. Optionally, a vehicle has a boiling point below 65° C. A vehicle is optionally present at a final concentration of about 5 percent to 40 percent w/w. Optionally, a vehicle is present at from 15 percent to 25 percent w/w. Optionally, a vehicle is present at 20% w/w. It is appreciated that more than one vehicle is optionally present in an inventive composition. Optionally, 2, 3, 4, 5, 6, or more vehicles are present in an inventive composition.

The inventive composition is optionally formulated with levels of organic solvent. An organic solvent is optionally volatile at ambient temperatures and pressures. Optionally, less than 35% organic solvent is included. Optionally, less than 30% organic solvent is included. Optionally, the level of volatile organic solvent is less than 15 percent w/w. Optionally, an organic solvent is present at 5% or less w/w. Optionally, an organic solvent is absent. An organic solvent is optionally an alcohol, illustratively ethanol. Optionally, an alcohol is an ethoxydiglycol, ethanol, or isopropyl alcohol. Optionally, an organic solvent is ethoxydiglycol present at 10 percent w/w or less. Optionally, ethoxydiglycol is present at 3 percent w/w. The level of organic solvent optionally does not induce noticeable drying or other toxic effects on the skin as opposed to the prior art that requires volatile organic solvents such as ethanol at much higher concentrations. It is appreciated that more than one organic solvent is optionally present in an inventive composition. It is further appreciated that the inventive composition be entirely ethanol free.

It is a particularly unexpected and surprising discovery of the subject invention that stable solutions of active compounds in the carrier can be prepared with less than 15 percent w/w organic solvent when combined with a vehicle at 5 percent to 40 percent w/w. It is particularly surprising that a vehicle at 5 percent to 40 percent w/w can promote a stable soluble solution with less than 5% organic solvent.

The inventive composition optionally includes other additives or pharmaceutical carriers illustratively including: stabilizers such as the anti-oxidant BHT; surfactants illustratively Laureth-4; anti-oxidants illustratively vitamins C and E, and Green tea extract (i.e. *Camellia sinensis*) or SILOX GT from Collaborative Labs, Stony Brook, N.Y.; and emollients illustratively the mixture or single components of the emollient sold under the brand name SYMREPAIR available from Symrise, Teterboro, N.J. One of ordinary skill in the art readily appreciates additives suitable for use with the present invention such as to provide desired flow characteristics, absorption, evaporation, delivery of active agent, conversion of a prodrug, or other desired characteristic.

The compositions of the invention are also optionally diluted to the appropriate active agent level for application by using other topically acceptable compounds or vehicles which are optionally miscible with the retinol or other active agent of the invention. Other cosmetic additives are optionally employed, either in the compositions of the invention or in those compositions when diluted with a suitable vehicle.

The compositions formulated as described herein are optionally topically applied to the skin on concentration which result in application of 0.005 to 1.0 weight percent retinol, optionally 0.01 to 0.50 weight percent. An active agent is optionally applied in the areas where fine lines, wrinkles, dry or inelastic skin or large pores are observed. Optionally, a moisturizer is applied with or after application of the inventive compositions to enhance the tactile comfort associated with application of the compositions and to enhance the wrinkle effacement and other benefits achieved by the compositions. An improved characteristic of the inventive composition is that the use of additional moisturizers is not required.

Optionally, moisturizing efficacy is achieved in the compositions of the present invention containing the retinol, thereby precluding the need for a separate moisturizer. Therefore, optional compositions of the invention are formulated to include moisturizing components that are compatible with the silicone carrier to a level of up to 35% by weight of the final formulation. Preferred moisturizing ingredients suitable for use the preferred compositions of the invention are illustratively petrolatum, ethylhexyl palmitate, cholesterol fatty acid ceramide, and squalene. The addition of one or more moisturizing components is beneficial when the inventive composition is applied to previously dried skin or under conditions where dryness commonly occurs such as in cold climates, or winter months. Optionally, a moisturizing component is applied where the active agent itself has a drying effect such as when retinol or 5-fluorouracil is applied.

With daily application of a retinol containing composition, skin texture, color and tone will improve. Wrinkles and fine lines will be reduced with minimal irritant effects.

An inventive composition is optionally applied to the skin of a subject. A subject is optionally a patient. A subject is optionally a mammal such as humans, non-human primates, horses, goats, cows, sheep, pigs, dogs, cats, and rodents.

An inventive composition is optionally provided as a lotion, cream, gel, bar, ointment, or in pad form. Optionally, the composition is provided in a single use container the contents of which are applied directly to the stratum corneum of a subject or applied to an applicator pad for subsequent delivery to the subject.

A cooling effect is optionally observed upon application of the inventive composition. Cooling effect as used herein means reducing the temperature of skin, optionally, from about 1 to about 2° C. upon application. The cooling effect includes the effect that results from carrier or vehicle evaporation.

The inventive composition is optionally administered one to three times daily. Optionally, the inventive composition is delivered once daily. Optionally, the inventive composition is administered weekly, biweekly, monthly, or any subdivision thereof. It is appreciated that the inventive composition be administered for an amount of time suitable for efficacy of the active agent. Optionally, the inventive composition is administered for one to six weeks. Optionally, the inventive composition is administered indefinitely.

Also provided is a process of formulating an inventive composition optionally for pleasing administration to the skin of a subject. An inventive process illustratively includes making a first solution by solubilizing one or more active agents optionally in an organic solvent preferably performed with gentle mixing in low to no light conditions.

A second solution is made by mixing additives such as emollients and vitamins. The second solution is added to and mixed with the first solution. Mixing is preferably in the dark under gentle mixing conditions.

A third solution of carrier and vehicle is made and the third solution is added to the combined first and second solutions to form a composition. Mixing is optionally non-vortex, gentle mixing in low light or darkness. Mixing is preferably for 120 minutes. The composition is preferably stored under inert gas such as nitrogen gas.

It is appreciated that low to no light conditions are important should light sensitive components be present in the subject invention. In the absence of light sensitive components, the inventive process is optionally performed in ambient or other lighting conditions.

The inventive process is optionally performed at ambient temperature and pressure conditions. Optionally, the inventive process is performed by heating one or more components or solutions.

Various aspects of the present invention are illustrated by the following non-limiting examples. The examples are for illustrative purposes and are not a limitation on any practice of the present invention. It will be understood that variations and modifications can be made without departing from the spirit and scope of the invention. One of ordinary skill in the art readily knows how to synthesize or commercially obtain the reagents and components described herein.

EXAMPLE 1

A Formula A composition is mixed containing 3.0 percent ethoxydiglycol, 0.5 percent Laureth-4, 0.10 percent hydroxypinnacolone retinoate, 0.05% BHT, 2.0 percent SYMREPAIR, 2.0 percent Tetrahexyldecyl ascorbate, 0.50 percent Tocopherol, 20 percent methoxynonafluorobutane, 1.0 percent SILOX GT, and the remainder Ethyl trisiloxane.

Formula A is prepared by creating solution 1 containing Ethoxydiglycol (Transcutol CG purchased from Gattefosse, Toronto, ON, Canada), Laureth-4 (Croda, Edison, N.J.), Hydrocypinnacolone retinoate (MDI-101, Concert LLC) and BHT by gentle mixing in a propeller mixer using low light conditions. Solution 2 is prepared separately. Solution 2 includes SYMREPAIR (Symrise, Inc., Teterboro, N.J.) which includes hexyldecanol, bisabolol, cetyl hydroxyproline palmitate, steric acid, and *Brassica campestris* sterols. SYMREPAIR is mixed with tetrahexyldecyl ascorbate (BV-OSC, Barnet, Englewood Cliffs, N.J.) and tocopherol USP in a propeller mixer until a clear solution forms. Solution 1 is combined with solution 2 by slow addition with continuous, non-vortex propeller mixing protecting the solutions from light. Solution 3 is prepared by gentle propeller mixing at ambient temperature. Solution 3 includes ethyltrisiloxane (Silsoft ETS, Monentiv, Albany, N.Y.), CF-61 (3M Specialty Materials) and SILOX GT (combination of cyclopentasiloxane and *Camellia sinesis* leaf extract from BASF Beauty Care). The combined solutions 1 and 2 are slowly added to solution 3 the continuous, non-vortex propeller mixing protected from the light. Mixing is continued for 120 minutes.

Formula A is transferred to opaque holding containers with nitrogen head-space for storage. 60 mL of Formula A is then transferred to 2 oz. amber glass bottles with a purified nitrogen gas head-space and stored protected from light until used.

A comparator solution is made containing 46.3% Cyclomethicone-Tetramer; 35% Alcohol SD 40B Anhydrous; 5% Ethylhexyl Palmitate; 5% Octyl Dimethyl PABA; 2% Benzophenone-3; 2% Demineralized Water; 2% Neopentyl Glycol Dicaprate; 1.5% Ethyl Cellulose K5000; 0.22% Butylated Hydroxytoluene; and 1% Retinoid Blend. Formula B is prepared essentially as described in U.S. Pat. No. 4,826,828, the contents of which are incorporated herein by reference.

EXAMPLE 2

A split face test is performed by using Formula A or the comparator as follows. Twelve females aged 20 to 59 apply Formula A to one side of their faces and comparator to the other side once daily for eight weeks. Thin shavings of the skin on each side of the face are taken before the test begins and after the eight week test period. The skin shavings after the test are in better condition than those before the test in all twelve women in the Formula A group and in nine of the twelve women in the comparator group. The skin of all women is both thicker and more organized after the test than before. All women in the Formula A group report improved moisture in the tested skin whereas the comparator group issues complaints of drying and cracking of the tested skin areas.

EXAMPLE 3

The ability of an electric current to flow through the stratum corneum provides an indirect measurement of the corneum's water content. The panelists who participated in the study in Example 2 are assessed for moisturization using an IBS impedance/conductance meter. At least twelve hours elapse between the last product application and the skin conductance measurement. The data demonstrate that the Formula A treated side is moister (higher conductance readings at all measurement time points) than comparator side. The comparator side of the face fails to show similar levels of relative moisture content. Thus, the objective measurement and substantiation of the stratum corneum's electrical conductivity shows a significant enhancement in facial skin moisture content.

EXAMPLE 4

A test of the ability of the Formula A composition of Example 1 relative to the comparator to reduce skin dryness is performed with or without supplemental moisturizer. Twelve panelists who demonstrate skin dryness upon repeated soap washing of the hands are selected to participate in this study. Initially, the panelists induce a condition of dryness by washing their hands with bar soap. The test formulations are applied daily to one hand while the other is left untreated to serve as a control side. Each hand is rated randomly by two trained evaluators who have no knowledge of which hand is treated. The evaluators use a stereomicroscope to assist them with their ratings. The results of this study demonstrate that the unmoisturized comparator side shows additional dryness compared to the control hand. This level of dryness is improved by application of moisturizer after each comparator application. In contrast, Formula A treated hands show marked improvement in moisture content. The addition of moisturizer after each Formula A application does not appreciably improve the treated skin moisture content. The Formula A benefits persist for twenty-four hours after the final treatment indicating that the Formula A composition provides effective long-lasting moisturization.

EXAMPLE 5

A Formula C solution is prepared wherein the active ingredient is benzoyl peroxide at 2.5 percent weight percent final. A phase 1 solution is prepared at ambient temperature by combining dimethyl isosorbide at 15% w/w final, ethanol (SD-Alcohol 40-B, 200 proof) at 4.7% w/w final, Laureth-4 at 1% w/w final, and benzoyl peroxide at 2.5% w/w final. The phase 1 ingredients are combined with continuous non-vortex propeller mixing.

Phase 2 is formed by combination of Methyl perfluorobutyl ether (and) Methyl perfluoroisobutyl ether (CF-61) at 35% w/w final and the remainder ethyl trisiloxane with continuous non-vortex propeller mixing until a clear solution is formed.

Phase 2 is slowly combined with phase 1 with continuous non-vortex propeller mixing. If a hazy solution is observed it will clarify upon standing for 24-48 hours at ambient temperature.

Formula C is stored in 60 ml volumes with absorbent applicator pads.

EXAMPLE 6

Patients presenting with acne to a dermatologist provide informed consent to a split face test comparing Formula C of Example 5 with a commercially available benzoyl peroxide topical acne treatment of equal active ingredient concentration (STRIDEX POWER PADS, Blistex, Inc. Oak Brook, Ill.).

Fifteen females aged 20 to 39 apply Formula C to one side of their faces and the benzoyl peroxide comparator to the other side once daily for two weeks. Each subject is asked to record any side effects such as dryness, irritation, and perceived skin clarification. Both the Formula C and the comparator demonstrate similar skin clarification. Subjects report less irritation and improved skin condition on the Formula C treated side relative to comparator.

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An active agent topical delivery composition comprising:
    an active agent present at a concentration between 0.001 to 0.5 weight percent, said active agent selected from the group consisting of vitamin A or its derivatives, salicylic acid, and benzoyl peroxide;
    a volatile linear organopolysiloxane carrier with 2 to 6 silicon atoms present at 10 percent to 75 percent by weight;
    a vehicle selected from the group consisting of methoxynonafluorobutane, ethoxynonafluorobutane, or a combination thereof, said vehicle present at from 5 percent to 40 percent by weight; and
    an alcohol at less than 5% by weight;
    said composition free of water and ethanol,
    wherein said active agent is insoluble at said concentration of active agent if in a fluid consisting of said active agent and said carrier or in a fluid consisting of said active agent and said vehicle, and wherein and the active agent fully soluble in the carrier and the vehicle combined at said concentration; and
    wherein the composition is clear liquid solution of said active agent at room temperature.

2. The composition of claim 1 wherein said alcohol is included and is ethoxydiglycol.

3. The composition of claim 1 wherein said active agent is a vitamin A derivative that is: retinal; retinoic acid; retinyl ester; retinol; tretinoin; isotretinoin; adapalene; tazarotene; or combinations thereof.

4. The composition of claim 1 wherein said active agent is vitamin A or its derivatives.

5. The composition of claim 1 wherein said agent is benzoyl peroxide, said benzyol peroxide present from 0.001 to 0.1 weight percent.

6. The composition of claim 1 wherein said volatile linear organopolysiloxane carrier is ethyl trisiloxane.

7. The composition of claim 6 wherein said ethyl trisiloxane is present at about 70 percent by weight.

8. The composition of claim 1 wherein said vehicle is present at 15 percent to 25 percent by weight.

9. The composition of claim 1 wherein said active agent is a retinoid.

10. The composition of claim 1, wherein said vehicle present at from 15 percent to 40 percent by weight.

11. The composition of claim 1, wherein the active agent is present at a concentration between 0.01 to 0.1 weight percent, wherein said volatile linear organopolysiloxane carrier is ethyl trisiloxane, and wherein said vehicle present at from 15 percent to 25 percent by weight.

12. A skin care composition comprising:
    a vitamin A or vitamin A derivative at a concentration between 0.01 to 0.5 weight percent;
    a volatile linear organopolysiloxane carrier of 2 to 6 silicon atoms present at 10 percent to 75 percent by weight;
    a vehicle selected from the group consisting of methoxynonafluorobutane, ethoxynonafluorobutane, or a combination thereof, said vehicle having a boiling point less than 78 degrees Celsius, said vehicle present at from 5 percent to 40 percent by weight; and
    an alcohol at 0-5 percent by weight;
    wherein said active agent is insoluble at said concentration if in a fluid consisting of said active agent and said carrier or in a fluid consisting of said active agent and said vehicle, and wherein and the active agent fully soluble in the carrier and the vehicle combined at said concentration;

said composition free of water and ethanol, and wherein the composition is clear liquid solution of said active agent at room temperature.

13. The composition of claim 12 wherein said active agent is vitamin A or its derivatives wherein said vitamin A or its derivatives are present at between 0.01 to 0.1 weight percent.

14. The composition of claim 12 wherein said volatile linear organopolysiloxane carrier is ethyl trisiloxane, or a combination of ethyl trisiloxane and disiloxane.

15. The composition of claim 14 wherein said ethyl trisiloxane is present at about 70 percent by weight.

16. The composition of claim 12 wherein said vehicle is present at 5 percent to 25 percent by weight.

17. The composition of claim 12, wherein said vehicle present at from 15 percent to 40 percent by weight.

18. The composition of claim 12, wherein the active agent is present at a concentration between 0.01 to 0.1 weight percent, wherein said volatile linear organopolysiloxane carrier is ethyl trisiloxane, and wherein said vehicle present at from 15 percent to 25 percent by weight.

19. The composition of claim 1 wherein said carrier is present at 70 percent by weight or greater, and said vehicle present at 15 to 25 percent by weight, said composition free of any additional agent capable of solublizing said active at said concentration.

* * * * *